United States Patent
Wang et al.

(10) Patent No.: US 11,061,010 B2
(45) Date of Patent: Jul. 13, 2021

(54) COAXIAL CAPACITIVE SENSOR AND A METHOD FOR ON-LINE MONITORING AND DIAGNOSING ENGINE LUBRICATING OIL ABRASIVE PARTICLES

(71) Applicant: XIAMEN UNIVERSITY, Xiamen (CN)

(72) Inventors: Yishou Wang, Xiamen (CN); Yancheng You, Xiamen (CN); Diheng Wu, Xiamen (CN); Tingwei Lin, Xiamen (CN); Xinlin Qing, Xiamen (CN); Hu Sun, Xiamen (CN)

(73) Assignee: XIAMEN UNIVERSITY, Xiamen (CN)

( * ) Notice: Subject to any disclaimer, the term of this patent is extended or adjusted under 35 U.S.C. 154(b) by 0 days.

(21) Appl. No.: 17/049,973

(22) PCT Filed: Mar. 17, 2020

(86) PCT No.: PCT/CN2020/079743
§ 371 (c)(1),
(2) Date: Oct. 23, 2020

(87) PCT Pub. No.: WO2020/207211
PCT Pub. Date: Oct. 15, 2020

(65) Prior Publication Data
US 2021/0132030 A1    May 6, 2021

(30) Foreign Application Priority Data
Apr. 9, 2019   (CN) .......................... 201910282282.1

(51) Int. Cl.
*G01N 33/28*   (2006.01)
*G01N 15/02*   (2006.01)
*G01N 27/22*   (2006.01)

(52) U.S. Cl.
CPC ..... *G01N 33/2888* (2013.01); *G01N 15/0266* (2013.01); *G01N 27/221* (2013.01); *G01N 33/2858* (2013.01)

(58) Field of Classification Search
CPC .......... G01N 33/2888; G01N 33/2858; G01N 15/0266; G01N 27/221
See application file for complete search history.

(56) References Cited

U.S. PATENT DOCUMENTS

2014/0203824 A1*  7/2014  Nivet ................... G01N 27/221
                                                                324/663

FOREIGN PATENT DOCUMENTS

| CN | 105571995 A | 5/2016 |
| CN | 109959587 A | 7/2019 |

(Continued)

OTHER PUBLICATIONS

Zhibin Han et al., Design and Implement of In-situ Capacitive Sensor for Monitoring Debris in the Lubricant Oil, Lubrication Engineering, 2018, vol. 43 No. 6.

*Primary Examiner* — Paul M. West
(74) *Attorney, Agent, or Firm* — Bayramoglu Law Offices LLC

(57) ABSTRACT

A coaxial capacitive sensor includes a sensor lubricating oil inlet and a sensor lubricating oil outlet. The sensor lubricating oil inlet and the sensor lubricating oil outlet separately communicate with the interior of the coaxial capacitive sensor. The interior of the coaxial capacitive sensor is provided with a center bearing, electrode support insulating substrates, and electrode plates. The plurality of electrode support insulating substrates and the center bearing divide the interior of the coaxial capacitive sensor into a plurality of detection sub-spaces, and the electrode plates are attached onto the electrode support insulating substrates, respectively. The coaxial capacitive sensor provided by the present (Continued)

invention can be arranged in a lubricating oil pipeline to avoid the influences of environmental factors on the testing results, and can on-line detect the characteristics of the lubricating oil abrasive particles efficiently.

18 Claims, 3 Drawing Sheets

(56) References Cited

FOREIGN PATENT DOCUMENTS

| | | |
|---|---|---|
| JP | 2007093570 A | 4/2007 |
| JP | 2012246778 A | 12/2012 |

* cited by examiner

COAXIAL CAPACITIVE SENSOR AND A METHOD FOR ON-LINE MONITORING AND DIAGNOSING ENGINE LUBRICATING OIL ABRASIVE PARTICLES

CROSS REFERENCE TO THE RELATED APPLICATIONS

This application is the national phase entry of International Application No. PCT/CN2020/079743, filed on Mar. 17, 2020, which is based upon and claims priority to Chinese Patent Application No. 201910282282.1, filed on Apr. 9, 2019, the entire contents of which are incorporated herein by reference.

TECHNICAL FIELD

The present invention relates to the field of aeroengine lubricating oil monitoring, in particular to a coaxial capacitive sensor and a method for on-line monitoring and diagnosing engine lubricating oil abrasive particles.

BACKGROUND

An aeroengine is a complex thermodynamic machine that works for long period of time under conditions of high temperature, high pressure, and high-speed rotation. During operation, the contact surfaces of various parts rub against each other, thereby generating large friction and causing internal loss of the engine. At the same time, the friction generates large amount of heat that overheats the parts, damaging the parts and causing the engine to malfunction. Therefore, lubricating oil is required to form an oil film on the surfaces of the parts in contact with each other to reduce friction.

In addition to the functions of lubrication and cooling, lubricating oil also acts as a transport medium for abrasive particles that are worn on the rolling and sliding surfaces. Abrasive particles are direct products of component wear rather than its secondary effects, and monitoring abrasive particles can reflect the severity of the wear state of the surfaces of friction pairs for life prediction. Thus, the technology of lubricating oil abrasive particle monitoring has great significance to effectively control the risk of engine wear and other failures and to ensure a safe and reliable operation of aircrafts.

In the prior art, lubricating oil abrasive particle monitoring methods are divided into two types: offline detection analysis and airborne online monitoring. The offline detection analysis requires collecting samples of lubricating oil in the engine and analyzing them by physical and chemical methods, mainly including spectral analysis and ferrographic analysis, while the airborne online monitoring generally uses capacitance, magnetic induction, ultrasound, inductance-capacitance (LC) resonance and other monitoring methods that can be integrated with the lubricating oil pipeline.

Off-line detection analysis is still widely used in aircraft detection because of its fast response, high precision, and rich abrasive particle characteristic information, but it is highly dependent on the equipment and experience of operators, and it cannot provide timely and effective feedbacks on the information. Different from off-line lubricating oil detection which requires the collection of samples, on-line monitoring depends on airborne sensors integrated in the engine lubricating oil system to collect real-time data and monitor abrasive particles through specific measurement principles.

From the perspective of physical effects, existing online monitoring methods for lubricating oil abrasive particles can be divided into three major types: an optical method, an electromagnetic method, and an energy method. The optical method can be further divided into a scattering method, a photometric method, and a direct imaging method. The optical method generally is closely integrated with graphic image analysis technology, and it has many types of detectable parameters. However, the optical method is easily affected by bubbles, and it is only suitable for occasions with low flow rates. The electromagnetic method can be further divided into a magnetic induction type, a resistance type, a capacitance type, a charge type, and an inductance type. The magnetic induction type is generally suitable for ferromagnetic abrasive particle monitoring, and the inductance type can distinguish ferromagnetic and non-ferromagnetic particles, while the capacitance type cannot distinguish metallic and non-metallic abrasive particles. The energy method mainly uses the indirect influence of abrasive particles in lubricating oil on mechanical resonance, pressure, microwave and other energy forms to monitor the concentration and compositions of abrasive particles. Generally, it is not suitable for monitoring the number and size of abrasive particles. In addition, traditional capacitive sensors accomplish online monitoring of lubricating oil abrasive particles typically by arranging electrodes on the outer surface of the lubricating oil pipeline. Consequently, the detection results are easily affected by environmental factors.

Reference "Design and Implement of In-situ Capacitive Sensor for Monitoring Debris in the Lubricant Oil", (HAN Zhibin et al. Vol. 43, No. 6, Lubrication Engineering, published on Jun. 30, 2018), discloses a coaxial capacitive sensor, which is a cylindrical sensor, that merely provides a direction for on-line direction, but cannot implement the effect of diagnosing the shape and size of abrasive particles in lubricating oil.

Therefore, how to utilize capacitive sensors to perform effective on-line monitoring and diagnosing on the number and size of lubricating oil abrasive particles has become a technical problem that needs to be solved in the technical field.

SUMMARY

In order to solve the above-mentioned problems identified in the prior art, the present invention provides a coaxial capacitive sensor, including a sensor lubricating oil inlet and a sensor lubricating oil outlet. The sensor lubricating oil inlet and the sensor lubricating oil outlet separately communicate with the interior of the coaxial capacitive sensor.

The interior of the coaxial capacitive sensor is provided with a center bearing, electrode support insulating substrates, and electrode plates. The plurality of electrode support insulating substrates and the center bearing divide the interior of the coaxial capacitive sensor into a plurality of detection sub-spaces, and the electrode plates are attached onto the electrode support insulating substrates, respectively.

On the basis of the above technical solution, furthermore, the coaxial capacitive sensor has a circular truncated cone configuration or a cylindrical configuration.

On the basis of the above technical solution, furthermore, the electrode plates include planar electrodes and curved electrodes to form planar non-parallel capacitors and curved parallel capacitors in the detection sub-spaces.

The present invention further provides a method for on-line monitoring and diagnosing engine lubricating oil abrasive particles using the coaxial capacitive sensor as mentioned above.

On the basis of the above technical solution, furthermore, the method includes the following steps:

step a: allowing lubricating oil carrying abrasive particles to enter the detection sub-spaces, and synchronously collecting monitoring signals of a plurality of capacitive sensors within different detection sub-spaces; and step b: extracting signal characteristics of two pairs of non-parallel capacitors from a time frequency domain to detect and diagnose morphological characteristics and quantitative characteristics of the abrasive particles.

On the basis of the above technical solution, furthermore, in step b, the detection sub-spaces detect and diagnose the morphological characteristics of the abrasive particles by using a correspondence relationship between the abrasive particles of different morphologies and signal characteristic changes.

On the basis of the above technical solution, furthermore, in step b, the detection sub-spaces perform quantitative monitoring and diagnosing on the number of the abrasive particles by identifying signal pulse changes generated when the abrasive particles pass.

On the basis of the above technical solution, furthermore, influences of environmental factors including temperature and flow rate on a diagnosis result are eliminated through a differential comparison and compensation of capacitive sensing signals in the plurality of detection sub-spaces of the coaxial capacitive sensor.

On the basis of the above technical solution, furthermore, a method of diagnosing and detecting a change of the mass of the lubricating oil abrasive particle is further included, which includes the following steps:

detecting a change $\Delta C$ of capacitance in combination with the coaxial capacitive sensor, and measuring a change $\Delta v$ of a medium flow rate and a change $\Delta t$ of a medium temperature;

marking the relationships between the capacitance and the medium flow rate, the medium temperature and the mass of the abrasive particle as: $C_v=f(v)$, $C_t=g(t)$, and $C_m=h(m)$, respectively;

changes of the capacitance caused by the above three factors being: $\Delta C_v=f(v+\Delta v)-f(v)$, $\Delta C_t=g(t+\Delta t)-g(t)$, and $\Delta C_m=h(m+\Delta m)-h(m)$, respectively; and obtaining $\Delta C_m=\Delta C-\Delta C_v-\Delta C_t$ to obtain the change of the mass of the abrasive particle.

Through ingenious design, the coaxial capacitive sensor provided by the present invention is arranged in a lubricating oil pipeline to avoid the influences of environmental factors on the testing results, and can on-line detect the quantitative and morphological characteristics of the lubricating oil abrasive particles efficiently through the cooperation of multiple sets of capacitors, thereby implementing the on-line monitoring for lubricating oil abrasive particles in the whole flow region, namely all flow regions of the lubricating oil pipeline, so as to reflect the severity of the wear state of the surfaces of friction pairs of engine rotating parts for life prediction to ensure a safe and reliable operation of the engine as an important practical application value.

The method for on-line monitoring and diagnosing engine lubricating oil abrasive particles cooperating with the coaxial capacitive sensor provided by the present invention establishes a coupling relationship between the morphological characteristics of the abrasive particles and capacitance changes to provide a basis for qualitative identification of the morphology of the abrasive particles. Preferably, the influences of environmental factors such as temperature and flow rate on the diagnosis result are eliminated through differential comparison and compensation of capacitive sensing signals of different detection sub-spaces.

BRIEF DESCRIPTION OF THE DRAWINGS

In order to explain the technical solutions of the embodiments of the present invention or technical solutions in the prior art more clearly, the drawings used in the description of the embodiments or the prior art will be introduced briefly below Obviously, the drawings that are described here are only some of the embodiments of the present invention, other figures may be obtained according to these figures by those having ordinary skill in the art without creative efforts.

Figure 1:
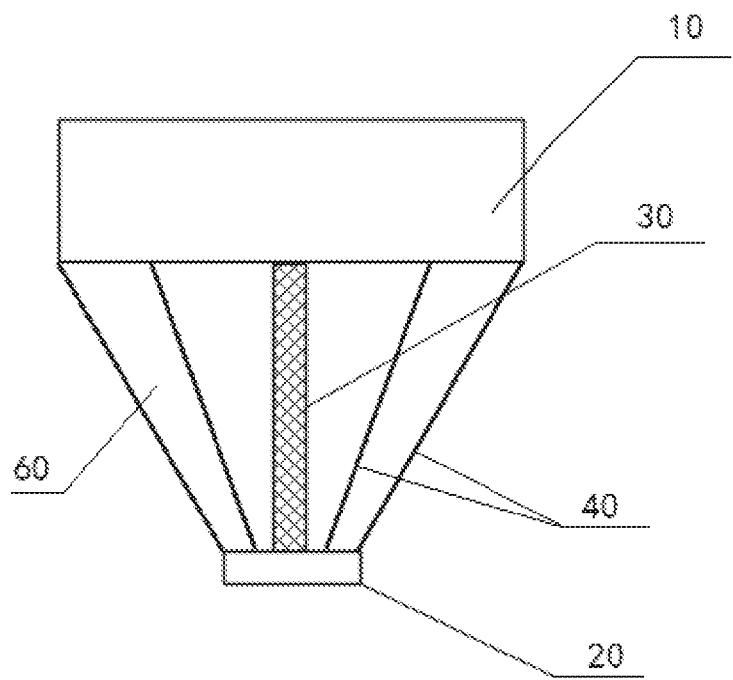
FIG. 1 is a structural schematic view of an embodiment of a circular truncated cone configuration sensor according to the present invention.

REFERENCE NUMERALS 10, sensor lubricating oil inlet; 20, sensor lubricating oil outlet; 30, center bearing; 40, electrode support insulating substrate; 50, electrode plate; 60, detection sub-space.

DETAILED DESCRIPTION OF THE EMBODIMENTS

Hereinafter, the technical solutions of the embodiments of the present application are described clearly and completely in combination with the drawings in the embodiments of the present application in order to make the objectives, technical solutions, and advantages of the embodiments of the present invention more clear. Obviously, the described embodiments are a part of the embodiments of the present invention rather than all the embodiments. Based on the embodiments of the present invention, all the other embodiments obtained by those having ordinary skill in the art without creative efforts shall fall within the scope of protection of the present invention.

In the description of the present invention, it should be explained that orientations or positional relationships indicated by terms "center", "longitudinal", "lateral", "upper", "lower", "front", "rear", "left", "right", "vertical", "horizontal", "top", "bottom", "in", "out" and so on are orientations and positional relationships shown based on the drawings, and merely used to facilitate the description of the present application and simplify the description, rather than indicating or implying that the device or element referred to must have a specific orientation and be configured or operated in a specific orientation, and thus cannot be construed as a limitation on the present application. In addition, the terms "first" and "second" are merely for descriptive purpose, and thus cannot be construed as indicating or implying relative importance.

Figure 2:
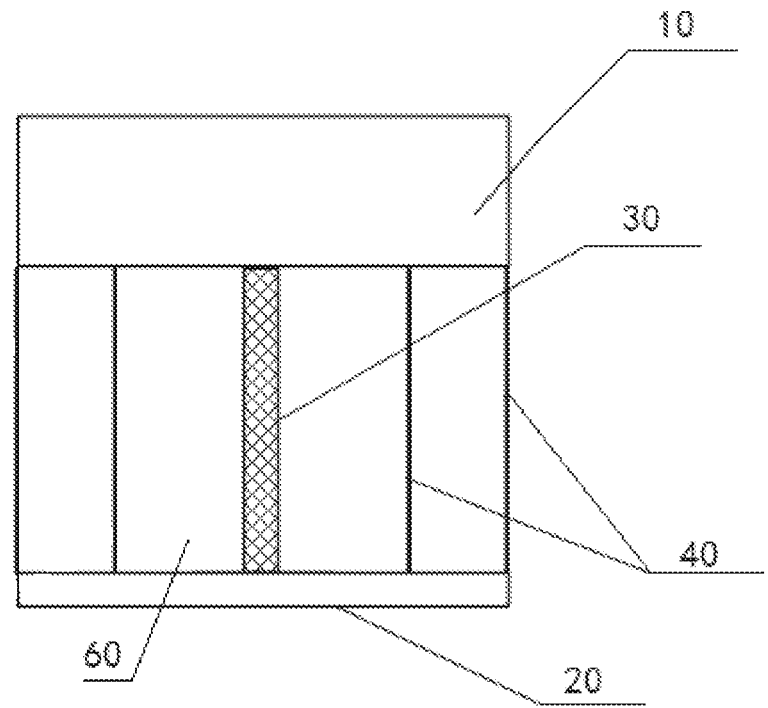
FIG. 2 is a structural schematic view of an embodiment of a cylindrical configuration sensor according to the present invention.
Figure 3:
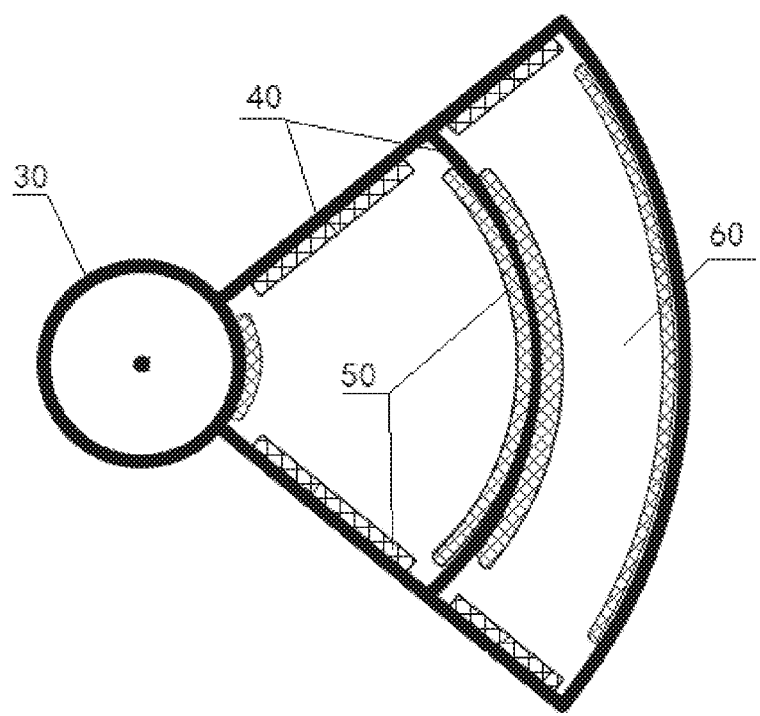
FIG. 3 is a schematic diagram of a detection sub-space in an embodiment of the present invention.

As shown in FIGS. 1-3, the present invention provides a coaxial capacitive sensor, including the sensor lubricating oil inlet 10 and the sensor lubricating oil outlet 20. The sensor lubricating oil inlet 10 and the sensor lubricating oil outlet 20 separately communicate with the interior of the coaxial capacitive sensor.

The interior of the coaxial capacitive sensor is provided with the center bearing 30, the electrode support insulating substrates 40, and the electrode plates 50. The plurality of electrode support insulating substrates 40 and the center bearing 30 divide the interior of the coaxial capacitive sensor into a plurality of detection sub-spaces 60. The electrode plates 50 are attached onto the electrode support insulating substrates 40, respectively.

Specifically, according to an embodiment as shown in FIG. 1, the coaxial capacitive sensor has a circular truncated cone configuration. According to another embodiment as shown in FIG. 2, the coaxial capacitive sensor has a cylindrical configuration. Optionally, coaxial capacitive sensors with other configurations can be further designed according to the specific needs based on the inventive concept of the present invention.

Figure 4:
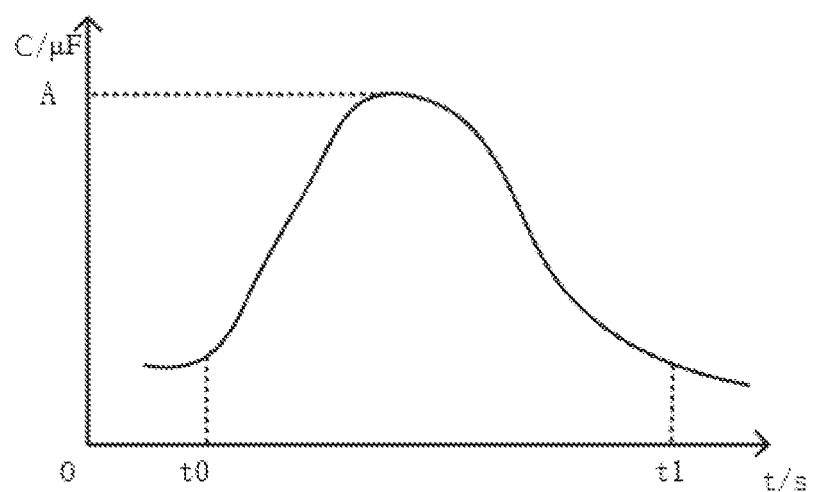
FIG. 4 is a first waveform diagram illustrating signal testing of a coaxial capacitive sensor according to the present invention.

As shown in FIGS. 1-6, the implementation of the coaxial capacitive sensor applied to on-line monitoring and diagnosing for aeroengine lubricating oil abrasive particles specifically includes the following steps:

lubricating oil carrying abrasive particles flows into the sensor lubricating oil inlet 10 through the detection sub-spaces 60 divided by the electrode support insulating substrates 40 and the center bearing 30, each of the detection sub-spaces 60 is provided with electrode plates 50, the electrode plates 50 include planar electrodes and curved electrodes, and the electrode plates 50 are attached onto the electrode support insulating substrates 40, respectively; the capacitors formed by the electrode plates 50 in the detection sub-spaces 60 detect the lubricating oil carrying the abrasive particles. Current signal processing techniques, such as wavelet transform, Fourier transform and the like, can be adopted for a plurality signals in the same detection sub-space to identify signal changes that are been generated when the abrasive particles pass. Specifically, the signal changes that are been generated after the processing are shown in FIG. 4, a pulse is used to indicate a debris passing through, accordingly, the number of the abrasive particles can be quantitatively counted.

Figure 5:
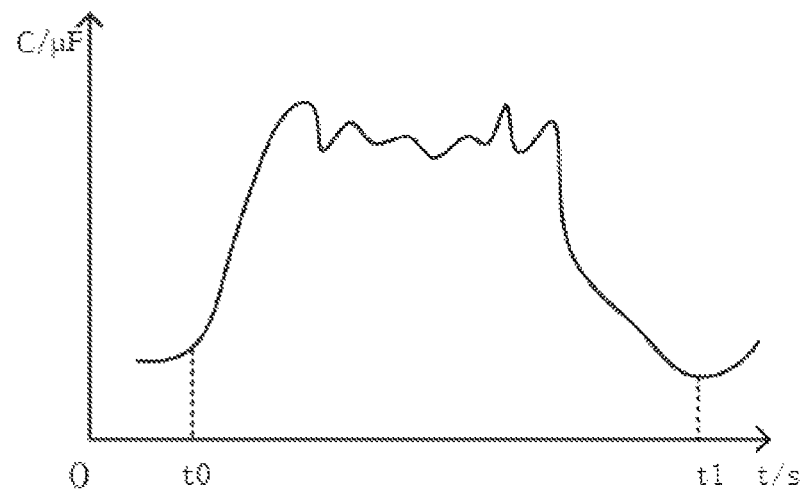
FIG. 5 is a second waveform diagram illustrating signal testing of the coaxial capacitive sensor according to the present invention.
Figure 6:
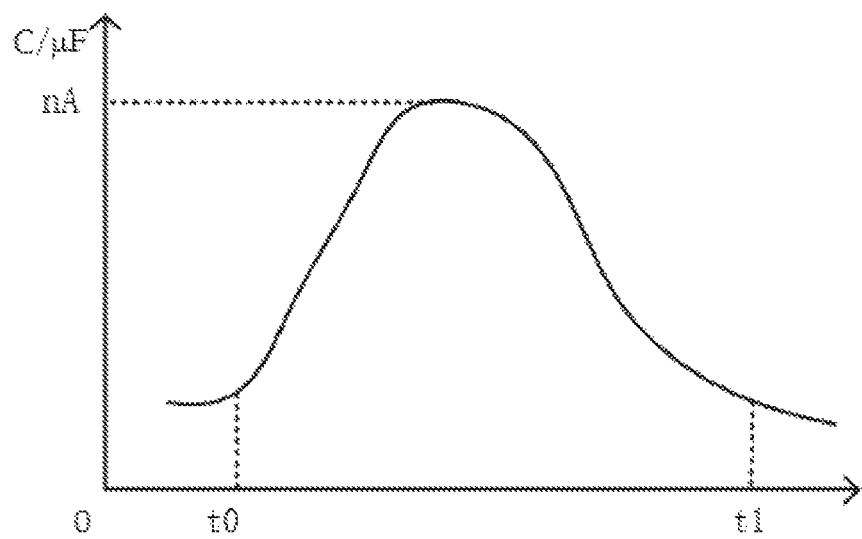
FIG. 6 is a third waveform diagram illustrating signal testing of the coaxial capacitive sensor according to the present invention.

On the basis of the above steps, characteristics of capacitance signals are further extracted from a time domain and a frequency domain, and signal characteristic changes are comprehensively utilized to qualitatively identify the morphology of the abrasive particles. Since the impact of the electric field on the wear particles, such as spherical, slender, and flat, flowing through the sensor's annular and reduced space of is different, different types of capacitive sensors (planar non-parallel capacitors and curved parallel capacitors) have different response signal characteristics (such as signal width, peak rate of change, etc.). As shown in FIGS. 4-6, by comparing FIG. 4 with FIG. 5, assuming that the time for the abrasive particles in the lubricating oil to pass through the sensor is t0-t1, within the same time, the shape of the abrasive particles can be roughly determined by observing the waveform of the abrasive particles (the abrasive particles will rotate when flowing through the sensor). The waveform of FIG. 4 is relatively flat, and the wave crest changes slowly, which indicate that the shape of the abrasive particles is roughly a spherical shape (the capacitance changes slightly during the rotation of the abrasive particles). The waveform of FIG. 5 has large fluctuations and the wave crest changes quickly, which indicate that the shape of the abrasive particles is roughly a slender or flat shape (the specific shape can be verified through experiment). FIG. 4 and FIG. 6 are waveforms detected by the capacitive sensors of different types when the same abrasive particle passes the same detection sub-space within the same time. The waveform of FIG. 4 is detected by a planar non-parallel capacitor, and the waveform of FIG. 6 is detected by a curved parallel capacitor. The waveforms of the two figures are substantially the same, and differ only in the waveform amplitude. Thus, multi-level fusion can be performed by utilizing the time domain signal characteristics obtained by different capacitive sensors in the same detection sub-space to establish correlation mapping or characterization of different morphological characteristics and signal characteristics of abrasive particles to further optimize and determine the different morphological characteristics of abrasive particles.

A coupling relationship between the morphological characteristics of the abrasive particles and the capacitance changes is established by the projection mapping of the abrasive particles of different morphologies on two pairs of electrode plates to provide a basis for qualitative identification of the morphology of the abrasive particles.

Influences of environmental factors such as temperature and flow rate on the diagnosis result can be eliminated through differential comparison and compensation of capacitive sensing signals of different detection sub-spaces. Specifically, the relationships between the capacitance and the medium flow rate, the medium temperature and the mass of the abrasive particle a $C_v=f(v)$, $C_t=g(t)$, and $C_m=h(m)$, respectively. After the medium flow rate, the medium temperature and the mass of the abrasive particle change by $\Delta v$, $\Delta t$ and $\Delta m$, respectively, the changes of the capacitance caused by the three factors are: $\Delta C_v=f(v+\Delta v)-f(v)$, $\Delta C_t=g(t+\Delta t)-g(t)$, and $\Delta C_m=h(m+\Delta m)-h(m)$, respectively. In the practical detection, the mass of the abrasive particle generated by engine wear is unknown, the parameters that can be detected include the change $\Delta v$ of the medium flow rate, the change $\Delta t$ of the medium temperature, and the change $\Delta C$ of the capacitance. According to experimental tests, there is a linear relationship between the capacitance and any one of the medium temperature, the flow rate and the mass of the abrasive particle, i.e., $\Delta C_m=\Delta C-\Delta C_v-\Delta C_t$. Accordingly, the change of the mass of the abrasive particle can be obtained, thereby implementing the diagnosing and monitoring of the abrasive particles.

INDUSTRIAL APPLICABILITY

Through ingenious design, the coaxial capacitive sensor provided by the present invention can be arranged in a lubricating oil pipeline to avoid the influences of environmental factors on the testing results and detects the quantitative and morphological characteristics of the lubricating oil abrasive particles efficiently through the cooperation of multiple sets of capacitors in real-time, thereby implementing on-line monitoring for lubricating oil abrasive particles in the whole flow region, that is, all flow regions of the lubricating oil pipeline, so as to reflect the severity of the wear state of the surfaces of friction pairs of engine rotating parts for life prediction to ensure a safe and reliable operation of the engine, which has important practical application value.

The coaxial capacitive sensor provided by the present invention can be applied to the method for on-line monitoring and diagnosing engine lubricating oil abrasive particles. When abrasive particles enter the sensor network, since the dielectric constant of the abrasive particles is much larger than the dielectric constant of the lubricating oil, the capacitance increases, pulse signals are generated, and the relative size of the abrasive particles can be detected by measuring the number and amplitude of the pulse signals.

Since the abrasive particles of different morphologies (such as spherical, slender, and flat) are differently affected by the electric field when flowing through the sensor's annular and reduced space, different types of capacitive sensors (equal-length non-parallel plate capacitors and unequal-length parallel plate capacitors) have different response signal characteristics (such as signal width, peak rate of change, etc.). Thus, the coaxial capacitive sensor provided by the present invention can determine the morphology of the abrasive particles through the response signal characteristics.

According to the coaxial capacitive sensor provided by the present invention, the interior of the lubricating oil abrasive particle sensor is divided into a plurality of flow detection sub-spaces using the electrode plates. Influences of environmental factors, such as temperature and flow rate on the diagnosis result, can be eliminated through differential comparison and compensation of capacitive sensing signals of different detection sub-spaces. The coaxial capacitive sensor network can be integrated with the lubricating oil pipeline to improve the accuracy without affecting the lubricating oil flow rate while ensuring the flow rate of the lubricating oil pipeline, which can implement the on-line monitoring of the lubricating oil abrasive particles in the whole flow region.

In addition, preferably, the coaxial capacitive sensor of the circular truncated cone configuration, the cylindrical configuration or the like can be integrated with the lubricating oil pipeline to improve its structural compatibility.

The method for on-line monitoring and diagnosing engine lubricating oil abrasive particles cooperating with the coaxial capacitive sensor provided by the present invention establishes a coupling relationship between the morphological characteristics of the abrasive particles and capacitance changes to provide a basis for qualitative identification of the morphology of the abrasive particles.

Preferably, the influences of environmental factors such as temperature and flow rate on the diagnosis result can be eliminated through differential comparison and compensation of capacitive sensing signals of different detection sub-spaces.

Although many terms such as sensor lubricating oil inlet, sensor lubricating oil outlet, center bearing, electrode support insulating substrate, electrode plate, detection sub-space and the like are used herein, the possibility of using other terms is not excluded. These terms are merely used to describe and explain the essence of the present invention more conveniently; and interpreting them as any kind of additional limitation is contrary to the spirit of the present invention.

Finally, it should be explained that the above various embodiments are merely used to illustrate the technical solution of the present invention, rather than to limit it. Although the present invention is illustrated in details by referring to the above various embodiments, those having ordinary skill in the art should understand: the technical solutions recited by the various embodiments described above can still be modified, or equivalent replacements can be made to a part or all of the technical features thereof, but these modifications or replacements do not make the essence of the corresponding technical solution depart from the scope of the technical solutions of the various embodiments of the present invention.

What is claimed is:

1. A coaxial capacitive sensor, comprising:
   a sensor lubricating oil inlet and a sensor lubricating oil outlet;
   wherein
   the sensor lubricating oil inlet and the sensor lubricating oil outlet separately communicate with an interior of the coaxial capacitive sensor;
   wherein the interior of the coaxial capacitive sensor is provided with a center bearing, a plurality of electrode support insulating substrates and a plurality of electrode plates;
   the plurality of electrode support insulating substrates and the center bearing divide the interior of the coaxial capacitive sensor into a plurality of detection sub-spaces;
   the plurality of electrode plates are attached onto the plurality of electrode support insulating substrates, respectively; and
   the plurality of electrode plates comprise a plurality of planar electrodes and a plurality of curved electrodes to form a plurality of planar non-parallel capacitors and a plurality of curved parallel capacitors in the plurality of detection sub-spaces.

2. The coaxial capacitive sensor of claim 1, wherein the coaxial capacitive sensor has a circular truncated cone configuration.

3. The coaxial capacitive sensor of claim 1, wherein the coaxial capacitive sensor has a cylindrical configuration.

4. A method for online monitoring and diagnosing engine lubricating oil abrasive particles using the coaxial capacitive sensor of claim 1, comprising:
   step a: allowing lubricating oil carrying the engine lubricating oil abrasive particles to enter the plurality of detection sub-spaces, and synchronously collecting monitoring signals of a plurality of capacitive sensors within the plurality of detection sub-spaces; and
   step b: extracting signal characteristics of two pairs of non-parallel capacitors from a time frequency domain to detect and diagnose morphological characteristics and quantitative characteristics of the engine lubricating oil abrasive particles.

5. The method of claim 4, wherein
   in step b, the plurality of detection sub-spaces detect and diagnose the morphological characteristics of the engine lubricating oil abrasive particles by using a correspondence relationship between the engine lubricating oil abrasive particles of different morphologies and changes of the signal characteristics.

6. The method of claim 4, wherein
   in step b, the plurality of detection sub-spaces perform quantitative monitoring and diagnosing on a number of the engine lubricating oil abrasive particles by identifying signal pulse changes generated when the engine lubricating oil abrasive particles pass.

7. The method of claim 4, wherein
   influences of environment factors comprising a temperature and a flow rate on a diagnosis result are eliminated through a differential comparison and compensation of capacitive sensing signals in the plurality of detection sub-spaces of the coaxial capacitive sensor.

8. The method of claim 4, further comprising a method for diagnosing and detecting a change of a mass of the engine lubricating oil abrasive particle, wherein the method for diagnosing and detecting the change of the mass of the engine lubricating oil abrasive particle comprises the following steps:
  detecting a change $\Delta C$ of a capacitance in combination with the coaxial capacitive sensor, and measuring a change $\Delta v$ of a medium flow rate and a change $\Delta t$ of a medium temperature;
  marking relationships between the capacitance and the medium flow rate, the medium temperature and the mass of the engine lubricating oil abrasive particle as: $C_v=f(v)$, $C_t=g(t)$, and $C_m=h(m)$, respectively;
  changes of the capacitance caused by the medium flow rate, the medium temperature and the mass of the engine lubricating oil abrasive particle being: $\Delta C_v=f(v+\Delta v)$, $\Delta C_t=g(t+\Delta t)-g(t)$, and $C_m=h(m+\Delta m)-h(m)$, respectively; and
  obtaining $\Delta C_m=\Delta C-\Delta C_v-\Delta C_t$ to obtain the change of the mass of the engine lubricating oil abrasive particle.

9. The method of claim 4, wherein
the coaxial capacitive sensor has a circular truncated cone configuration.

10. The method of claim 9, wherein
in step b, the plurality of detection sub-spaces detect and diagnose the morphological characteristics of the engine lubricating oil abrasive particles by using a correspondence relationship between the engine lubricating oil abrasive particles of different morphologies and changes of the signal characteristics.

11. The n od of claim 9, wherein
in step b, the plurality of detection sub-spaces perform quantitative monitoring and diagnosing on a number of the engine lubricating oil abrasive particles by identifying signal pulse changes generated when the engine lubricating oil abrasive particles pass.

12. The method of claim 9, wherein
influences of environment factors comprising a temperature and a flow rate on a diagnosis result are eliminated through a differential comparison and compensation of capacitive sensing signals in the plurality of detection sub-spaces of the coaxial capacitive sensor.

13. The method of claim 9, further comprising a method for diagnosing and detecting a change of a mass of the engine lubricating oil abrasive particle, wherein the method for diagnosing and detecting the change of the mass of the engine lubricating oil abrasive particle comprises the following steps:
  detecting a change $\Delta C$ of a capacitance in combination with the coaxial capacitive sensor, and measuring a change $\Delta v$ of a medium flow rate and a change $\Delta t$ of a medium temperature;
  marking relationships between the capacitance and the medium flow rate, the medium temperature and the mass of the engine lubricating oil abrasive particle as: $C_v=f(v)$, $C_t=g(t)$, and $C_m=h(m)$, respectively;
  changes of the capacitance caused by the medium flow rate, the medium temperature and the mass of the engine lubricating oil abrasive particle being: $\Delta C_v=f(v+\Delta v)$, $\Delta C_t=g(t+\Delta t)-g(t)$, and $\Delta C_m=h(m+\Delta m)-h(m)$, respectively; and
  obtaining $\Delta C_m=\Delta C-\Delta C_v-\Delta C_t$ to obtain the change of the mass of the engine lubricating oil abrasive particle.

14. The method of claim 4, wherein
the coaxial capacitive sensor has a cylindrical configuration.

15. The method of claim 14, wherein
in step b, the plurality of detection sub-spaces detect and diagnose the morphological characteristics of the engine lubricating oil abrasive particles by using a correspondence relationship between the engine lubricating oil abrasive particles of different morphologies and changes of the signal characteristics.

16. The method of claim 14, wherein in step b, the plurality of detection sub-spaces perform quantitative monitoring and diagnosing on a number of the engine lubricating oil abrasive particles by identifying signal pulse changes generated when the engine lubricating oil abrasive particles pass.

17. The method of claim 14, wherein
influences of environment factors comprising a temperature and a flow rate on a diagnosis result are eliminated through a differential comparison and compensation of capacitive sensing signals in the plurality of detection sub-spaces of the coaxial capacitive sensor.

18. The method of claim 14, further comprising a method for diagnosing and detecting a change of a mass of the engine lubricating oil abrasive particle, wherein the method for diagnosing and detecting the change of the mass of the engine lubricating oil abrasive particle comprises the following steps:
  detecting a change $\Delta C$ of a capacitance in combination with the coaxial capacitive sensor, and measuring a change $\Delta v$ of a medium flow rate and a change $\Delta t$ of a medium temperature;
  marking relationships between the capacitance and the medium flow rate, the medium temperature and the mass of the engine lubricating oil abrasive particle as: $C_v=f(v)$, $C_t=g(t)$, and $C_m=h(m)$, respectively;
  changes of the capacitance caused by the medium flow rate, the medium temperature and the mass of the engine lubricating oil abrasive particle being: $\Delta C_v=f(v+\Delta v)-f(v)$, $\Delta C_t=g(t+\Delta t)-g(t)$, and $\Delta C_m=h(m+\Delta m)-h(m)$, respectively; and
  obtaining $\Delta C_m=\Delta C-\Delta C_v-\Delta C_t$ to obtain the change of the mass of the engine lubricating oil abrasive particle.

* * * * *